United States Patent
Halasa et al.

(10) Patent No.: US 7,671,237 B2
(45) Date of Patent: Mar. 2, 2010

(54) SYNTHESIS OF SOLUBLE FUNCTIONALIZED LITHIUM INITIATORS

(75) Inventors: Adel Farhan Halasa, Bath, OH (US); Wen-Liang Hsu, Cuyahoga Falls, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 674 days.

(21) Appl. No.: 11/479,717

(22) Filed: Jun. 30, 2006

(65) Prior Publication Data
US 2006/0252861 A1    Nov. 9, 2006

Related U.S. Application Data

(60) Division of application No. 10/713,122, filed on Nov. 14, 2003, now Pat. No. 7,166,747, and a continuation-in-part of application No. 10/713,122, filed on Nov. 14, 2003, now Pat. No. 7,166,747, which is a division of application No. 09/944,664, filed on Aug. 31, 2001, now Pat. No. 6,686,504.

(60) Provisional application No. 60/229,494, filed on Aug. 31, 2000.

(51) Int. Cl.
C07C 221/00    (2006.01)
C07C 225/00    (2006.01)
C08C 19/22    (2006.01)

(52) U.S. Cl. .................... 564/305; 564/328; 564/329; 525/351

(58) Field of Classification Search .................. None
See application file for complete search history.

(56) References Cited

U.S. PATENT DOCUMENTS

| | | | |
|---|---|---|---|
| 4,158,098 A | 6/1979 | Trepka | 568/633 |
| 4,196,154 A | 4/1980 | Tung et al. | 260/665 R |
| 5,521,309 A | 5/1996 | Antkowiak et al. | 540/612 |
| 5,981,639 A | 11/1999 | Hsu et al. | 524/394 |
| 6,221,975 B1 * | 4/2001 | Shin et al. | 525/351 |
| 6,518,214 B2 * | 2/2003 | Halasa et al. | 502/108 |

* cited by examiner

Primary Examiner—Daniel M Sullivan
Assistant Examiner—Clinton Brooks
(74) Attorney, Agent, or Firm—Alvin T. Rockhill

(57) ABSTRACT

This invention discloses a process for making dilithium initiators in high purity. This process can be conducted in the absence of amines which is desirable since amines can act as modifiers for anionic polymerizations. The dilithium compounds made are highly desirable because they are soluble in aromatic solvents. The present invention also discloses a tire which is comprised of a generally toroidal-shaped carcass with an outer circumferential tread, two spaced beads, at least one ply extending from bead to bead and sidewalls extending radially from and connecting said tread to said beads, wherein said tread is adapted to be ground-contacting, and wherein said tread is a cured the rubber formulation which is comprised of (a) at least one rubbery polymer containing functional groups of the structural formula:

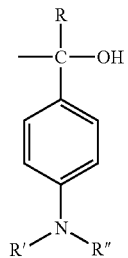

wherein R, R' and R" can be the same or different, wherein R is selected from the group consisting of hydrogen atoms, alkyl groups, aryl groups, alkaryl groups, and amino aryl groups, and wherein R' and R" represent alkyl groups alkyl groups that contain from 1 to 8 carbon atoms, and (b) at least one member selected from the group consisting of carbon black and silica.

20 Claims, No Drawings

SYNTHESIS OF SOLUBLE FUNCTIONALIZED LITHIUM INITIATORS

This is a divisional and a continuation-in-part application of U.S. patent application Ser. No. 10/713,122, filed on Nov. 14, 2003 (now issued as U.S. Pat. No. 7,166,747), which is a divisional of U.S. patent application Ser. No. 09/944,664, filed on Aug. 31, 2001 (now issued as U.S. Pat. No. 6,686, 504), which claims the benefit of the priority of U.S. Provisional Patent Application Ser. No. 60/229,494, filed on Aug. 31, 2000.

BACKGROUND OF THE INVENTION

Lithium compounds are commonly used as initiators for anionic polymerizations. Such organolithium initiators can be employed in synthesizing a wide variety of rubbery polymers. For instance, organolithium initiators can be used to initiate the anionic polymerization of diolefin monomers, such as 1,3-butadiene and isoprene, into rubbery polymers. Vinyl aromatic monomers can, of course, also be copolymerized into such polymers. Some specific examples of rubbery polymers that can be synthesized using organolithium compounds as initiators include polybutadiene, polyisoprene, styrene-butadiene rubber (SBR), styrene-isoprene rubber, and styrene-isoprene-butadiene rubber (SIBR).

The organolithium compounds that can be used to initiate such anionic polymerizations can be either a specific organomonolithium compound or it can be a multifunctional type of initiator. In commercial applications monolithium compounds are normally used because they are available as pure compounds that are soluble in organic solvents. Multifunctional organolithium compounds are not necessarily specific compounds but rather represent reproducible compositions of regulable functionality. Many of such multifunctional organolithium compounds must be stored under refrigeration before being used.

U.S. Pat. No. 5,981,639 explains that multifunctional initiators used to initiate anionic polymerizations include those prepared by reacting an organomonolithium compounded with a multivinylphosphine or with a multivinylsilane, such a reaction preferably being conducted in an inert diluent such as a hydrocarbon or a mixture of a hydrocarbon and a polar organic compound. The reaction between the multivinylsilane or multivinylphosphine and the organomonolithium compound can result in a precipitate which can be solubilized if desired, by adding a solubilizing monomer such as a conjugated diene or monovinyl aromatic compound, after reaction of the primary components. Alternatively, the reaction can be conducted in the presence of a minor amount of the solubilizing monomer. The relative amounts of the organomonolithium compound and the multivinylsilane or the multivinylphosphine preferably should be in the range of about 0.33 to 4 moles of organomonolithium compound per mole of vinyl groups present in the multivinylsilane or multivinylphosphine employed.

U.S. Pat. No. 5,981,639 further notes such multifunctional initiators are commonly used as mixtures of compounds rather than as specific individual compounds. Other multifunctional polymerization initiators can be prepared by utilizing an organomonolithium compound, further together with a multivinylaromatic compound and either a conjugated diene or monovinylaromatic compound or both. These ingredients can be charged initially, usually in the presence of a hydrocarbon or a mixture of a hydrocarbon and a polar organic compound as a diluent. Alternatively, a multifunctional polymerization initiator can be prepared in a two-step process by reacting the organomonolithium compound with a conjugated diene or monovinyl aromatic compound additive and then adding the multivinyl aromatic compound. Any of the conjugated dienes or monovinyl aromatic compounds described can be employed. The ratio of conjugated diene or monovinyl aromatic compound additive employed preferably should be in the range of about 2 to 15 moles of polymerizable compound per mole of organolithium compound. The amount of multivinylaromatic compound employed preferably should be in the range of about 0.05 to 2 moles per mole of organomonolithium compound. Exemplary multivinyl aromatic compounds include 1,2-divinylbenzene, 1,3-divinylbenzene, 1,4-divinylbenzene, 1,2,4-trivinylbenzene, 1,3-divinylnaphthalene, 1,8-divinylnaphthalene, 1,3,5-trivinylnaphthalene, 2,4-divinylbiphenyl, 3,5,4'-trivinylbiphenyl, m-diisopropenyl benzene, p-diisopropenyl benzene, 1,3-divinyl-4,5,8-tributylnaphthalene and the like. Divinyl aromatic hydrocarbons containing up to 18 carbon atoms per molecule are preferred, particularly divinylbenzene as either the ortho, meta or para isomer and commercial divinylbenzene, which is a mixture of the three isomers, and other compounds, such as the ethylstyrenes, also is quite satisfactory.

U.S. Pat. No. 4,196,154 discloses organic liquid soluble multifunctional lithium containing initiators are prepared by reacting an organo lithium compound with an organic compound containing at least one group of the configuration 1,3-bis(1-phenylethenyl)benzene. U.S. Pat. No. 4,196,154 reports that such initiators can be prepared in the absence of polar solvents and are very desirable for the polymerization of dienes such as butadiene to a desirable 1,4 configuration.

SUMMARY OF THE INVENTION

This invention discloses a process for making dilithium initiators in high purity. This process can be conducted in the absence of amines which is desirable since amines can act as modifiers for anionic polymerizations. The dilithium compounds made are highly desirable because they are soluble in aromatic solvents and do not need to be stored under refrigeration.

The present invention more specifically discloses a process for synthesizing a dilithium initiator which comprises reacting diisopropenylbenzene with a tertiary alkyl lithium compound in an aromatic solvent at a temperature which is within the range of about 0° C. to about 100° C.

The present invention further discloses a process for synthesizing m-di-(1-lithio-1-methyl-3,3-dimethylbutyl)benzene which comprises reacting diisopropenylbenzene with tertiary-butyllithium in an aromatic solvent at a temperature which is within the range of about 0° C. to about 100° C.

The subject invention also discloses a process for synthesizing a functionalized lithium initiator which comprises the steps of (1) reacting diisopropenylbenzene with a tertiary alkyl lithium compound in an aromatic solvent at a temperature which is within the range of about 0° C. to about 100° C. to produce a dilithium initiator; and (2) reacting the dilithium initiator with a halide compound selected from the group consisting of (a) tin halides of the structural formula:

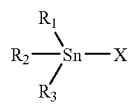

(b) silicon halides of the structural formula:

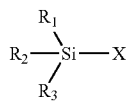

(c) amine halides of the structural formula:

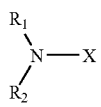

and (d) phosphorus halides of the structural formula:

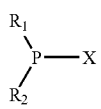

wherein X represents a halogen atom, and wherein R1, R2, and R3 can be the same or different and represent alkyl groups, aryl groups, or alkoxy groups containing from 1 to about 10 carbon atoms.

The present invention also discloses a process for synthesizing a functionalized lithium initiator which comprises the steps of (1) reacting diisopropenylbenzene with a tertiary alkyl lithium compound in an aromatic solvent at a temperature which is within the range of about 0° C. to about 100° C. to produce a dilithium initiator; and (2) reacting the dilithium initiator with a compound having the structural formula:

$$R_2 \underset{R_3}{\overset{R_1}{-}}\!\!\!\!\!\!\!\!\!\!\!\!\!\!\!\!\!\!\!\!\!\!\!\!\!\!\!\!\!\!\!-X$$

wherein X represents a neucleophile, and wherein R1, R2, and R3 can be the same or different and represent alkyl groups, aryl groups, or alkoxy groups containing from 1 to about 10 carbon atoms. The neucleophile will typically be selected from the group consisting of aldehydes, ketones, esters, halides, and acetals. Halides are typically preferred.

The present invention further discloses a process for synthesizing a functionalized lithium initiator which comprises the steps of (1) reacting diisopropenylbenzene with a tertiary alkyl lithium compound in an aromatic solvent at a temperature which is within the range of about 0° C. to about 100° C. to produce a dilithium initiator; and (2) reacting the dilithium initiator with a alkylaminoaryl compound of the structural formula:

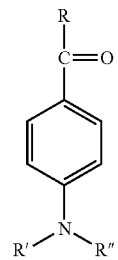

wherein R, R', and R" can be the same or different, wherein R is selected from the group consisting of hydrogen atoms, alkyl groups, aryl groups, alkaryl groups, and amino aryl groups, and wherein R' and R" represent alkyl groups.

The present invention also reveals a process for synthesizing a functionalized lithium initiator which comprises reacting a dilithium initiator with an alkylaminoaryl compound of the structural formula:

wherein R, R', and R" can be the same or different, wherein R is selected from the group consisting of hydrogen atoms, alkyl groups, aryl groups, alkaryl groups, and amino aryl groups, and wherein R' and R" represent alkyl groups.

DETAILED DESCRIPTION OF THE INVENTION

Dilithium initiators can be synthesized using the process of this invention by reacting a tertiary-alkyl lithium compound with m-diisopropenylbenzene in an aromatic solvent. The aromatic solvent will typically be an alkyl benzene. The alkyl group in the alkyl benzene will typically contain from 1 to 8 carbon atoms. It is preferred for the alkyl group in the alkyl benzene solvent to contain from 1 to about 4 carbon atoms. Some preferred aromatic solvents include toluene, ethyl benzene, and propyl benzene. Ethyl benzene is the most highly preferred aromatic solvent.

It is critical for a tertiary-alkyl lithium compound to be reacted with the m-diisopropenylbenzene. The tertiary-alkyl lithium compound will typically contain from 4 to about 8 carbon atoms. It is preferred for the tertiary-alkyl lithium compound to be tertiary-butyl lithium.

The reaction will typically be conducted at a temperature that is within the range of about 0° C. to about 100° C. It is normally preferred for the reaction between the tertiary-alkyl lithium and the m-diisopropenylbenzene to be carried out at a temperature that is within the range of about 10° C. to about 70° C. It is typically more preferred for the reaction temperature to be within the range of about 20° C. to about 40° C.

A functionalized lithium initiator can be prepared by reacting a dilithium initiator with a halide compound. Any dilithium initiator can be employed. However, dilithium initiators that are synthesized by reacting a tertiary-alkyl lithium compound with m-diisopropenylbenzene are highly preferred. The halide compound utilized will be selected from the group consisting of (a) tin halides of the structural formula:

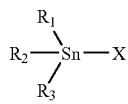

(b) silicon halides of the structural formula:

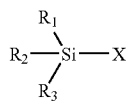

(c) amine halides of the structural formula:

(d) phosphorus halides of the structural formula:

and (e) halides of the structural formula:

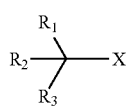

wherein X represents a halogen atom, and wherein R1, R2, and R3 can be the same or different and represent alkyl groups, aryl groups, or alkoxy groups containing from 1 to about 10 carbon atoms. R1, R2, and R3 will typically be alkyl groups containing from 1 to about 4 carbon atoms or alkoxy groups containing from 1 to 4 carbon atoms. It is preferred for R1, R2, and R3 to be methyl groups (CH3-), ethyl groups (CH3-CH2-), methoxy groups (CH3-O—), or ethoxy groups (CH3-CH2-O—).

A compound of the structural formula:

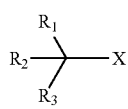

wherein X represents a neucleophile, and wherein R1, R2, and R3 can be the same or different and represent alkyl groups, aryl groups, or alkoxy groups containing from 1 to about 10 carbon atoms, can be reacted with the dilithium initiator in place of the halide compounds described above. In such compounds the neucleophile will typically be selected from the group consisting of aldehydes, ketones, esters, halides, and acetals. Halides are typically preferred neucleophiles.

The alkylaminoaryl compounds that can be reacted with the dilithium compound are typically of the structural formula:

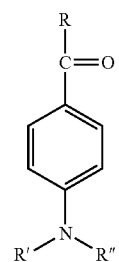

wherein R, R', and R" can be the same or different, wherein R is selected from the group consisting of hydrogen atoms, alkyl groups, aryl groups, alkaryl groups, and amino aryl groups, and wherein R' and R" represent alkyl groups. It is typically preferred for R' and R" to represent alkyl groups that contain from 1 to about 8 carbon atoms. It is generally more preferred for R' and R" to represent alkyl groups that contain from 1 to about 4 carbon atoms, such as methyl groups, ethyl groups, propyl groups, and butyl groups. Highly preferred alkylaminoaryl compounds that can be utilized are of the structural formula:

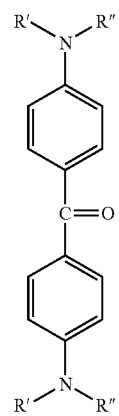

wherein R' and R" can be the same or different and wherein R' and R" represent alkyl groups. Some highly preferred alkylaminoaryl compounds include N,N-dimethylaminobenzaldehyde and 4,4'-bis(dimethylamino)benzophenone.

The functionalization reaction will typically be carried out at a temperature that is within the range of about −80° C. to about 150° C. However, to enhance the probability of monofunctionalization, which reduces the probability of di-functionalization, the functionalization reaction will preferably be carried out at a reduced temperature. It is accordingly preferred for the functionalization reaction to be conducted at a temperature that is within the range of about −70° C. to about 20° C. It is normally more preferred for the functionalization reaction to be conducted at a temperature that is within the range of about −60° C. to about 0° C. It is also preferred for the halide compound to be added to a solution of the dilithium initiator (rather than adding the dilithium initiator to the halide compound).

The functionalized initiators made by utilizing the technique of this invention offer significant advantages when used to initiate the anionic polymerization of diene monomers, such as 1,3-butadiene or isoprene, into rubbery polymers. For instance, such functionalized initiators offer improved solubility in aliphatic solvents. More importantly, the rubbery polymers made with such functionalized initiators offer improved compatibility in rubber formulations that contain silica and/or carbon black. Such rubbery polymer can optionally be coupled with tin and/or silicon compounds. For instance, such rubbery polymers can be coupled with tin tetrachloride or silicon tetrachloride.

The synthesis of functionalized lithium initiators by the process of this invention by reacting a dilithium initiator with an alkylaminoaryl compound can be depicted as follows:

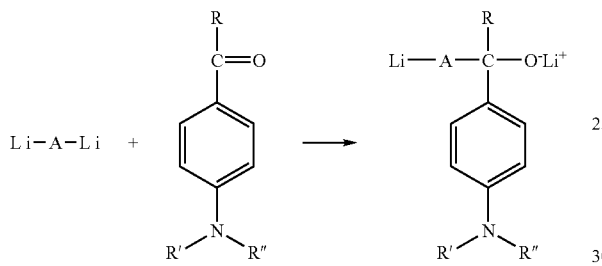

wherein A represents a hydrocarbon moiety, and wherein R, R', and R" can be the same or different, wherein R is selected from the group consisting of hydrogen atoms, alkyl groups, aryl groups, alkaryl groups, and amino aryl groups, and wherein R' and R" represent alkyl groups.

The functionalized initiator made by this process can then be utilized in the polymerization of conjugated diolefin monomers, such as 1,3-butadiene or isoprene, or optionally the copolymerization of conjugated diolefin monomers with vinyl aromatic monomers, such as styrene or α-methyl styrene. Anionic polymerizations that are conducted utilizing such monomers can be depicted as follows:

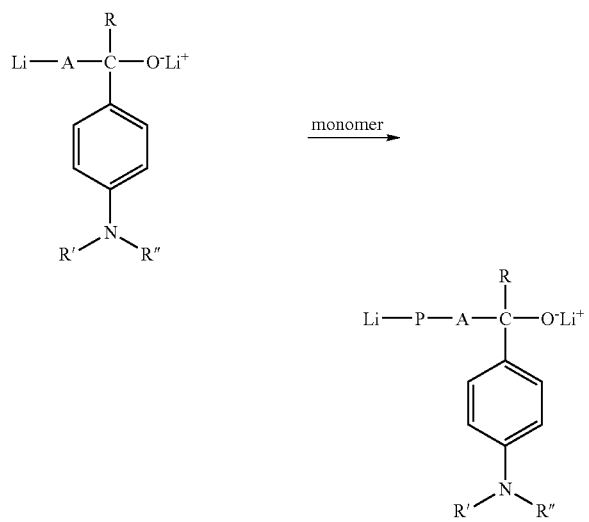

wherein P represents the polymer chain made by the polymerization, wherein A represents a hydrocarbon moiety, wherein R, R', and R" can be the same or different, wherein R is selected from the group consisting of hydrogen atoms, alkyl groups, aryl groups, alkaryl groups, and amino aryl groups, and wherein R' and R" represent alkyl groups.

The living polymer made by this process can be killed by exposure to water or an alcohol. The reaction of such polymers with water can be depicted as follows:

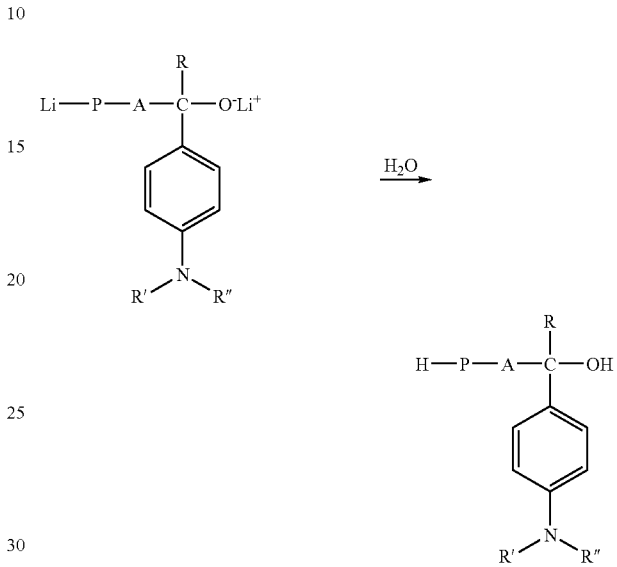

Accordingly, the functionalized rubbery polymers made by the process of this invention contain functional groups of the structural formula:

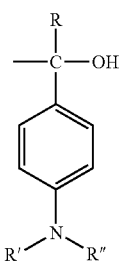

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLE 1

In this example, a stable and hydrocarbon soluble dilithio initiator was prepared. Neat m-diisoprenylbenzene (100 mmoles) was added, under nitrogen, to a dried quart (0.95 liter) bottle containing 400 ml of reagent grade ethylbenzene at room temperature. Then tert-butyllithium (in hexanes) was added in four portions of 50 mmoles with constant shaking. It was left at room temperature for two hours after the addition of the tert-butyllithium was completed. The bottle containing the reaction mixture was then rotated in a polymerization bath at 65° C. bath for two hours. After removing it from the bath, it was left to cool at room temperature. The resulting reddish brown solution containing dilithio initiator was titrated using the Gilman double titration method for active lithium. The GC-MS analysis of the hydrolyzed (with D20) product indicated that more than 95% dilithio species was formed.

EXAMPLE 2

In this experiment, the dilithium compound synthesized by the procedure described in Example 1 was used to initiate the polymerization of 1,3-butadiene monomer into polybutadiene rubber. In the procedure used, 2300 g of a silica/amumina/molecular sieve dried premix containing 20 weight percent of 1,3-butadiene in hexanes was charged into a one-gallon (3.8 liters) reactor. Then, 19.6 ml of 0.234 M dilithio initiator (Di-Li) was added to the reactor. The target number averaged molecular weight (Mn) was 100,000.

The polymerization was carried out at 75° C. for two hours. The GC analysis of the residual monomers contained in the polymerization mixture indicated that the 100% of monomer was converted to polymer. The polymerization was then shortstopped with ethanol and the polymer cement was then removed from the reactor and stabilized with 1 phm of antioxidant. After evaporating hexanes, the resulting polymer was dried in a vacuum oven at 50° C.

The polybutadiene produced was determined to have a glass transition temperature (Tg) at −99° C. It was also determined to have a microstructure, which contained 8 percent 1,2-polybutadiene units, 92 percent 1,4-polybutadiene units. The Mooney viscosity (ML-4) at 100° C. for this polymer was also determined to be 44. It was determined by GPC to have a number average molecular weight (Mn) of 193,000 and a weight average molecular weight (Mw) of 198,000. The MWD (Mw/Mn) of this polymer was 1.03. This example clearly validated the formation of dilithio species in the Example I since the molecular weight of the polymer was double of the target value.

EXAMPLE 3

In this example, a telechlic functionalized polybutadiene containing 4,4'-bis(diethylamino) benzophenol functional groups on both polymer chain ends was prepared. The procedure described in Example 2 was utilized in these examples except that two molar quantity (to Di-Li) of 4,4'-bis(diethylamino) benzophenone was added to the live cement after the polymerization of 1,3-butadiene was completed. The Tg and microstructures of this functionalized PBd were identical to polymer made in Example 2. The Mooney viscosity (ML-4) at 100° C. for this polymer was 48.

EXAMPLE 4

In this example, a telechlic functionalized styrene-butadiene rubber (SBR) containing tributyl tin groups on both polymer chain ends was prepared. The procedure described in Example 2 was utilized in these examples except that a premix containing styrene/1,3-butadiene in hexanes was used as the monomers and the styrene to 1,3-butadiene ratio was 15:85. In addition, 0.75 molar ratio of TMEDA (N,N,N',N'-tetramethylethylenediamine) to di-lithium was used as the modifier. Two molar quantities (to di-lithium) of t-butyltin chloride was added to the live cement after the polymerization of styrene/1,3-butadiene was completed. The glass transition temperature (Tg) of this functionalized SBR was determined to be −45° C. The Mooney viscosity (ML-4) at 100° C. for this polymer was determined to be 45.

EXAMPLE 5

In this example, a telechlic tin-coupled styrene-butadiene rubber (SBR) at both polymer chain ends was prepared. The procedure described in Example 4 was utilized in this example except that the target number average molecular weight (Mn) was 75,000 instead of 100,000. Tin tetrachloride was added the live cement after the polymerization of styrene/1,3-butadiene was completed. The Tg of this functionalized SBR was determined to be −45° C. The Mooney viscosity (ML-4) at 100° C. for the coupled SBR was 88 while the uncoupled base polymer (precursor prior to coupling) was 30.

EXAMPLE 6

In this experiment, 1000 grams of a silica/amumina/molecular sieve dried premix of styrene and 1,3-butadiene in hexanes containing 20 weight percent monomer was charged into a one-gallon (3.8 liter) reactor. The ratio of styrene to 1,3-butadiene was 20:80. Copolymerization was initiated by charging sodium dedecylbenzene sulfonate and the dilithium initiator made in Example 1 to the reactor at a molar ratio of 0.25:1. The copolymerization was allowed to continue at 70° C. until all of the-monomer was consumed (for about one hour). Then an additional 1000 grams of monomer premix and N,N,N',N'-tetramethylethylene-diamine (TMEDA) was charged into the reactor containing the living polymer cement. The monomer premix added contained 40% styrene and 60% 1,3-butadiene. The molar ratio of TMEDA to dilithium initiator was 5:1. The copolymerization was allowed to continue at 70° C. for an additional hour until the monomers were essentially exhausted. Then the copolymerization was shortstopped and the polymer was stabilized by the addition of an antioxidant. The SBR made was then recovered and dried in a vacuum oven. The SBR had two glass transition temperatures at −75° C. (center block) and −20° C. (outer blocks).

EXAMPLE 7

In this example, a soluble functionalized lithium initiator containing trimethyltin groups was prepared. In the procedure used, 34 ml of 1 M of trimethyltin chloride (in hexane) was added with a syringe to a quart (0.95 liter) bottle containing 200 ml of 0.34 M 1,3-bis(1-lithio-1,3,3'-trimethylbutyl) benzene (in ethyl benzene). The mixture was shaken at room temperature for about two hours. The resulting mono-lithio initiator, 1-(1-lithio-1,3,3'-trimethylbutyl)-3-(1-trimethyltin-1,3,3'-trimethylbutyl)benzene was determined by Gilman titration to be 0.13 M.

EXAMPLES 8-10

In these examples, soluble mono-lithio initiators containing tributyltin, tributylsilyl, 2-(N,N-dimethylamino)ethyl functional groups were prepared using the same procedures as described in Example 7 except that that tributyltin chloride, tributylsilicon chloride and 2-(N,N-dimethylamino) ethyl chloride were use in place of trimethyltin chloride.

EXAMPLE 11

In this experiment, a polybutadiene containing a trimethyltin functional group was prepared. In the procedure used, 2300 g of a silica/amumina/molecular sieve dried premix containing 20 weight percent of 1,3-butadiene in hexanes was charged into a one-gallon (3.8 liters) reactor. 35.3 ml of 0.13

M a mono functionalized initiator, 1-(1-lithio-1,3,3'-trimethylbutyl)-3-(1-trimethyl tin-1,3,3'-trimethylbutyl)benzene was added to the reactor. The target number averaged molecular weight (Mn) was 100,000.

The polymerization was carried out at 75° C. for 2.5 hours. The GC analysis of the residual monomers contained in the polymerization mixture indicated that the 100% of monomer was converted to polymer. The polymerization was then shortstopped with ethanol and the polymer cement was then removed from the reactor and stabilized with 1 phm of antioxidant. The polymer was then recovered by evaporation of the hexanes solvent. The resulting polymer was dried in a vacuum oven at 50° C.

The polybutadiene produced was determined to have a glass transition temperature (Tg) at −99° C. It was also determined to have a microstructure that contained 9 percent 1,2-polybutadiene units and 91 percent 1,4-polybutadiene units. The Mooney viscosity (ML-4) at 100° C. for this polymer was also determined to be 55.

EXAMPLE 12

In this example, a soluble functionalized lithium initiator containing dimethylaminophenyl was prepared. 34 ml. of 1 M p-dimethylaminobenzaldehyde (in toluene) was added, via a syringe, to a quart bottle containing 200 ml. of 0.34 M 1,3-bis(1-lithio-1,3,3-trimethylbutyl) benzene (in cyclohexane) at room temperature. The mixture was shaken at room temperature for an hour. The resulting mono-lithio initiator, 1-(1-lithio-1,3,3-trimethylbutyl)-3-(1-(p-dimethylaminophenyl, lithioxy)methyl)-1,3,3-trimethylbutyl)benzene was determined by Gilman titration to be 0.15 M.

EXAMPLE 13

In this example, a soluble mono-lithio initiators containing bis-(dimethylaminophenyl) functional groups was prepared using the same procedure as described in Example 12 except that 4,4'-bis-(dimethylamino)benzophenone (Michler's ketone) was used in place of p-dimethylamino benzaldehyde.

EXAMPLE 14

In this experiment, a 15/85 styrene-butadiene rubber (SBR) containing a 1-(4-dimthylaminophenyl)-1-hydroxymethyl functional group was prepared. 2300 g of a silica/amumina/molecular sieve dried premix containing 20 weight percent of 1,3-butadiene and styrene in hexanes was charged into a one-gallon (3.8 liters) reactor. The ratio of styrene to 1,3-butadiene was 15:85. 16.1 ml. of 0.15 M a mono functionalized initiator, 1-(1-lithio-1,3,3-trimethylbutyl)-3-(1-(p-dimethylaminophenyl, lithioxy)methyl)-1,3,3-trimethylbutyl)benzene was added to the reactor. The target number averaged molecular weight (Mn) was 200,000.

The polymerization was carried out at 70° C. for 1.5 hours. The GC analysis of the residual monomers contained in the polymerization mixture indicated that the 100% of monomer was converted to polymer. The polymerization was then shortstopped with ethanol and the polymer cement was then removed from the reactor and stabilized with 1 phm of antioxidant. After the hexanes solvent, the resulting polymer was dried in a vacuum oven at 50° C.

The SBR produced was determined to have a glass transition temperature (Tg) at −38° C. It was also determined to have a microstructure, which contained 52 percent 1,2-polybutadiene units, 33 percent 1,4-polybutadiene units and 15% random polystyrene units. The Mooney viscosity (ML-4) at 100° C. for this polymer was also determined to be 73.

While certain representative embodiments and details have been shown for the purpose of illustrating the subject invention, it will be apparent to those skilled in this art that various changes and modifications can be made therein without departing from the scope of the subject invention.

What is claimed is:

1. A tire tread rubber composition which is comprised of (a) at least one rubbery polymer which is synthesized using a functionalized lithium initiator, wherein the functionalized initiator is made by a process which comprises (i) reacting m-diisopropenylbenzene with a tertiary alkyl lithium compound in an aromatic solvent at a temperature which is within the range of about 0° C. to about 100° C. to produce a dilithium initiator and (ii) reacting the dilithium initiator with an alkylaminoaryl compound of the structural formula:

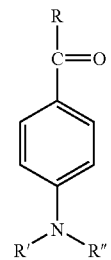

wherein R, R', and R" can be the same or different, wherein R is selected from the group consisting of hydrogen atoms and alkyl groups, and wherein R' and R" represent alkyl groups, and (b) at least one member selected from the group consisting of carbon black and silica.

2. A tire tread rubber composition as specified in claim 1 wherein said rubbery polymer is coupled with at least one member selected from the group consisting of silicon halides and tin halides.

3. A tread rubber composition as specified in claim 1 wherein R represents a hydrogen atom and wherein R' and R" represent methyl groups.

4. A tread rubber composition as specified in claim 1 wherein the alkyl groups contain from 1 to about 8 carbon atoms.

5. A tread rubber composition as specified in claim 1 wherein the alkyl groups contain from 1 to about 4 carbon atoms.

6. A tire tread rubber composition which is comprised of (a) at least one rubbery polymer which is synthesized using a functionalized lithium initiator, wherein the functionalized initiator is made by a process which consists of reacting a dilithium initiator with an alkylaminoaryl compound of the structural formula:

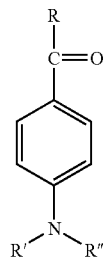

wherein R, R', and R" can be the same or different, wherein R is selected from the group consisting of hydrogen atoms and alkyl groups, and wherein R' and R" represent alkyl groups, and (b) at least one member selected from the group consisting of carbon black and silica.

7. A tire tread rubber composition as specified in claim 6 wherein the dilithium initiator is made by (i) reacting m-diisopropenylbenzene with a tertiary alkyl lithium compound in an aromatic solvent at a temperature which is within the range of about 0° C. to about 100° C.

8. A tire tread rubber composition as specified in claim 7 wherein R represents a hydrogen atom.

9. A tire tread rubber composition as specified in claim 7 wherein R represents an alkyl group.

10. A tire tread rubber composition as specified in claim 8 wherein R' and R" represent methyl groups.

11. A tire tread rubber composition as specified in claim 1 wherein the member selected from the group consisting of carbon black and silica is silica.

12. A tire tread rubber composition as specified in claim 6 wherein the member selected from the group consisting of carbon black and silica is silica.

13. A tire tread rubber composition as specified in claim 1 wherein the m-diisopropenylbenzene is reacted with the tertiary alkyl lithium compound at a temperature which is within the range of about 10° C. to about 70° C.

14. A tire tread rubber composition as specified in claim 1 wherein the m-diisopropenylbenzene is reacted with the tertiary alkyl lithium compound at a temperature which is within the range of about 20° C. to about 40° C.

15. A tire tread rubber composition as specified in claim 1 wherein said rubbery polymer is coupled a silicon halide.

16. A tire tread rubber composition as specified in claim 1 wherein said rubbery polymer is coupled a tin halide.

17. A tire tread rubber composition as specified in claim 16 wherein the tin halide is of the structural formula:

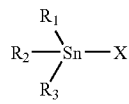

wherein X represents a halogen atom, and wherein $R_1$, $R_2$, and $R_3$ can be the same or different and represent alkyl groups, aryl groups, or alkoxy groups containing from 1 to about 10 carbon atoms.

18. A tire tread rubber composition as specified in claim 15 wherein the silicon halide is of the structural formula:

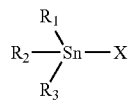

wherein X represents a halogen atom, and wherein $R_1$, $R_2$, and $R_3$ can be the same or different and represent alkyl groups, aryl groups, or alkoxy groups containing from 1 to about 10 carbon atoms.

19. A tire tread rubber composition as specified in claim 17 wherein $R_1$, $R_2$, and $R_3$ represent alkyl groups containing from 1 to about 4 carbon atoms or alkoxy groups containing from 1 to 4 carbon atoms.

20. A tire tread rubber composition as specified in claim 17 wherein $R_1$, $R_2$, and $R_3$ are selected from the group consisting of methyl groups, ethyl groups, methoxy groups, and ethoxy groups.

* * * * *